(12) United States Patent
Ricci et al.

(10) Patent No.: US 6,582,228 B2
(45) Date of Patent: Jun. 24, 2003

(54) SURGICAL IMPLANT SYSTEM, ARTICLE AND KIT

(76) Inventors: John L. Ricci, 46 Verdun Pl., Middleton, NJ (US) 07748; Harold Alexander, 47 Elmwood Pl., Short Hills, NJ (US) 07078; Bruce Hollander, 312 S. Military Trail, Boca Raton, FL (US) 33442; Ingo Kozak, 312 S. Military Trail, Atlantis, FL (US) 33442

( * ) Notice: Subject to any disclaimer, the term of this patent is extended or adjusted under 35 U.S.C. 154(b) by 130 days.

(21) Appl. No.: 09/766,064

(22) Filed: Jan. 22, 2001

(65) Prior Publication Data

US 2001/0032022 A1 Oct. 18, 2001

Related U.S. Application Data

(63) Continuation-in-part of application No. 09/187,584, filed on Nov. 6, 1998, now Pat. No. 6,224,635.

(51) Int. Cl.[7] .................................................. A61C 8/00
(52) U.S. Cl. ........................ 433/173; 623/23.56; 623/2; 427/2.24
(58) Field of Search ............................ 623/23.56, 23.61, 623/23.62, 16, 165, 11.11, 66.1; 433/173; 423/311, 308; 424/422, 423; 106/124, 173.01; 427/2.24, 2.27; 514/300, 256

(56) References Cited

U.S. PATENT DOCUMENTS

| | | | | |
|---|---|---|---|---|
| 5,147,403 A | * | 9/1992 | Gitelis | 128/898 |
| 5,336,264 A | * | 8/1994 | Constanz et al. | 423/308 |
| 5,462,722 A | * | 10/1995 | Liu et al. | 423/305 |
| 6,224,635 B1 | * | 5/2001 | Ricci et al. | 424/426 |

* cited by examiner

Primary Examiner—Paul Prebilic
Assistant Examiner—Crystal Gilpin
(74) Attorney, Agent, or Firm—M. K. Silverman; Yi Li

(57) ABSTRACT

A surgical implant system includes an implant body and an osseostimulative surface applied to, or used with, the implant body, the surface including a calcium sulfate (CS) compound which is a member selected from the group consisting of CS dihydrate, CS hemihydrate, anhydrous CS, and mixtures thereof. The performance and rate of resorption of the osseostimulative surface may be improved or modified through the use of a stabilizing component, a viscosity modifier, a pH modifier, or a cell growth inductive microgeometry. The system is also definable in terms of an in situ system of bone augmentation in which a bio-resorbable CS matrix, in various physical forms, from a kit is disposed about the surgical implant positioned within an osseotomy site.

9 Claims, 3 Drawing Sheets

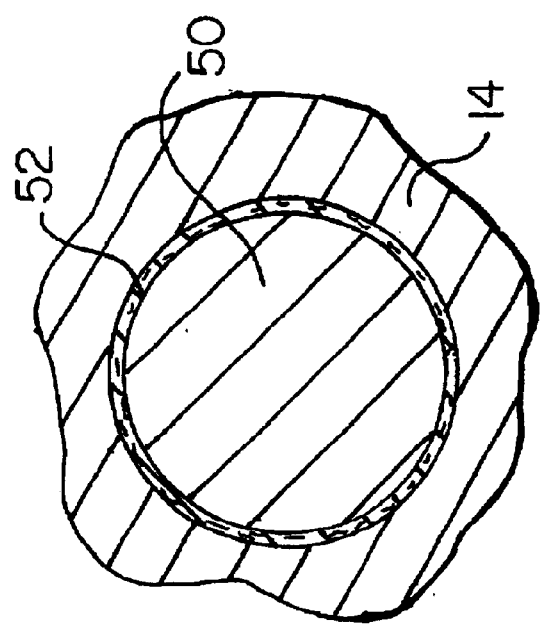
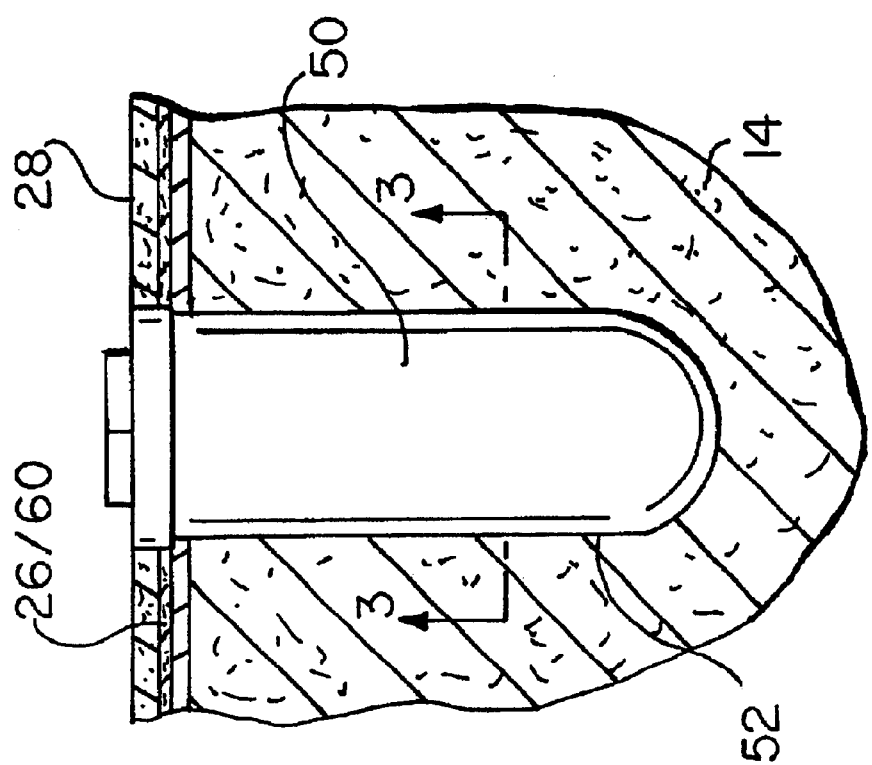

SURGICAL IMPLANT SYSTEM, ARTICLE AND KIT

REFERENCE TO RELATED APPLICATION

This case is a continuation-in-part of application Ser. No. 09/187,584, filed Nov. 6, 1998 by Ricci, et al, now U.S. Pat. No. 6,224,635, issued May 1, 2001 entitled Implantation of Surgical Implants with Calcium Sulfate, the subject matter of which is incorporated herein by reference.

BACKGROUND OF THE INVENTION

1. Field of Invention

The instant invention relates to surgical implants and related systems for use with surgical implants, inclusive of orthopedic and dental implants for the purpose of enhanced osseo-integration of the implant into the surgical site to further post-operative efficacy of the implant-related procedure. The present invention is particularly of interest in use with metallic implants such as those of titanium, titanium alloy, titanium/aluminum/vanadium alloy, zirconium and tantalum and metallic implants coated with an osseo-simulative material such as hydroxyapatite.

2. Dental Implants

There exist many implants; each designed for a specific function. Most are made of titanium, an inert metal which has been proven to be effective at fusing with living bone, a process known as "osseointegration." The cylindrical or screw type implant called "root form" is similar in shape to the root of a tooth with a surface area designed to promote good attachment the bone. It is the most widely used design and generally placed where there is plentiful width and depth of jawbone. Where the jawbone is too narrow or short or immediate placement of root form implants the area may be enhanced with bone grafting to allow for their placement.

When the jawbone is to narrow and is a good candidate for bone grafting, a special narrow implant, called " plate form," can be placed into the bone, i.e., in cases of advanced bone loss, such a subperiosteal implant may be prescribed. It rests on top of the bone but under the gums.

The actual implant procedure involves the surgical placement of an implant, a healing period (osseointegration), and implant restoration to replace the missing tooth or teeth. The treatment may be a cooperative effort between a surgical dentist who actually places the implant and a restorative dentist who designs, prescribes and inserts the final replacement teeth. Some dentists having advanced training provide both of these services.

Root form implants are the closest in shape and size to the natural tooth root. They are commonly used in wide, deep bone to provide a base for replacement of one, several, or a complete arch of teeth. After application of an anesthetic, the dentist will expose the area of the jawbone to be implanted and prepare the bone to accept the implant. The number of incisions and manner of bone preparation depends upon the number of implants (and teeth) to be replaced. The implant is carefully set into place and the gums are closed with several stitches. The healing period usually varies from three to six months. During this time osseointegration occurs. The bone grows in and around the implant creating a strong structural support. In fact, this bond can be even stronger than the original tooth's. When healing is complete, the implant is uncovered and an extension or abutment is attached to it. At that time, the implant and abutment act as a solid unit ready to support the patient's new tooth or teeth.

3. Orthopedic Implants

Owing to the rapid development of surgery, it is now possible to carry out operations to bones and joints which were recently inconceivable. For example, it is now possible to carry out surgical removal of cysts, foci of suppuration in bone, and several of malignant tumors from bones. This results in defects in the bone, which need to be filled since normal bone repair processes are no longer able to compensate them. Some defects of this type may have a volume of up to 600 cm to be filled.

For filling cavities of this type use is made of bone replacement materials in liquid, pasty or a solid form such as granules or implants for implantation. If the cavities which are to be filled are not too large, then the purpose of the bone replacement materials is to temporarily fill the cavities in the bone and to allow the body itself to compensate, in the course of time, for the defect with living bone material.

4. Bio-compatible Materials

Bone implants are frequently used in surgical procedures, which are implanted in the bones of the body of a recipient and permanently replace parts of the skeleton or roots of teeth. The outer layer of the bone implant, which comes into contact with the living substrate bone, is termed the bone-contact layer. At the present time, metals, such as, for example, special steels, noble metals, titanium, ceramic materials, such as, for example, alumina,. glass-ceramics, hydroxy-apatite ceramics and synthetic materials are used as bone implants and as bone-contact layers.

These substances are classified as biocompatible and bioactive according to the tissue compatibility. Biocompatible substances are tolerated by the body in the long term without rejection. Bioactive substances become rigidly incorporated like endogenous tissue, the tissue compatibility determined by the chemical composition, the crystalline structure, the surface structure and the mechanical properties.

The metals and some ceramic materials such as, for example, alumina ceramics, are biocompatible. Ensheathing by connective tissue always takes place in the body. This connective tissue layer allows the implant to be held relatively rigidly, but does not allow frictional connection to the mineral framework of the substrate bone.

Because of the absence of primary integration into the substrate bone, a biocompatible implant of this type can be exposed to only slight mechanical stress since otherwise it is held poorly, which is associated with pain and, finally, the loss of the implant. This is found, for example, with hip joint prostheses which are always subject to great stress and for which more than one quarter of the operations are carried out are because of loosening of an implant which had previously been inserted.

Thus, additional undercutting such as, for example, a screw thread is necessary for permanent mechanical anchoring of biocompatible implants in bone. With all metallic implants it is still an unanswered question of whether they release toxic metal ions into the surroundings and thus may have adverse effects in the long term. Even when bone cement is used, despite the initially better mechanical connection to the substrate bone, the loosening above described takes place, although with some delay.

In about the last twenty (20) years, implant techniques that employ many artificial hard tissue materials have been used surgeons. Among these materials, bioglass and bioceramics, such as hydroxyapatite and beta-tricalcium phosphate, have excellent biocompatibility. Most of the bioglass and bioceramics for medical applications are prepared either in granule or block form. The granule form has mobility problems and relatively poor manipulation characteristics, while the block form is quite brittle and difficult to shape. Many other techniques have been attempted to solve the above-noted problems. Various of these techniques have employed other materials such as: plaster of paris (calcium sulfate), CS hemihydrate, collagen, different types of calcium phosphate grout or cement, polylactates and polyacrylate cement compositions. None of these have been completely acceptable.

5. Desired Parameters

The surgeon is often interested in implant techniques that employ materials that can be shaped and hardened in situ. Ideally, an effective implant technique should employ a surgical cement or binder system for hard tissue applications, having the following characteristics: good biocompatibility, a suitable resorption rate, moldable at the surgical site, and controllable setting time and characteristics.

Most currently techniques employing available surgical cements and binder composition system have disadvantages. For example, collagen-hydroxyapatite and polylactate-hydroxyapatite composites can only be made as premolded shapes and cannot be molded at the surgical site.

Generic plaster of paris, which is derived from gypsum, has reasonable setting characteristics but its resorption rate is too fast. Polyacrylate cement is non-resorbable. Polyacrylic acid-calcium phosphate cement is not resorbable and the setting cement is too acidic. Most of the calcium phosphate grouts or cement composition are prepared by the reaction of calcium phosphate ceramics with an acidic component. See, for example, Bajpai, U.S. Pat. No. 4,663, 295. In general, these cement compositions are disadvantageously acidic in nature and take too long to reach a neutral pH. The calcium phosphate grouts or cement compositions either lack satisfactory mechanical strength or are resorbed too slowly. Moreover, most prior art calcium phosphate cement compositions developed require the use of hydroxyapatite or tricalcium phosphate as the cementing ceramic and phosphoric acid, a bifunctional organic acid or other polyfunctional organic acids as a setting reagent. These cement compositions are also very acidic in nature and take too long to reach a neutral pH. Also, after implantation, these cement compositions may cause irritation and inflammatory reactions. Thus, surgical techniques employing these materials have not proven to be totally satisfactory.

Biocompatibility has also been a limiting factor in successful application of implant cement compositions The most successful artificial implant materials to achieve the excellent biocompatibility have been hydroxyapatite, bioglass, and other calcium phosphate ceramics. Bioglass is a bioactive glass material whose major components are $CaO$, $SiO_2$ and $P_2O$. Minor components may be $Na_2O$, $MgO$, $Al_23$, $B_2O_3$ and $CaF_2$. A bioactive glass can form a surface layer of hydroxyapatite when soaked in an aqueous environment. Hydroxyapatite with beta-tricalcium phosphate ceramics and calcium phosphate containing glass have been extensively studied. Clinical studies confirmed that most of the calcium phosphate ceramics such as hydroxyapatite, tricalcium phosphate, tetra calcium phosphate, and dicalcium phosphate have excellent biocompatibility and are well accepted by both hard tissue and soft tissue. Experimental results also indicate that dense hydroxyapatite is nonbioresorbable while other porous calcium phosphate ceramics are bioresorbable. However, surgical techniques employing these materials have not proven satisfactory 6. Calcium Sulfate ("CS")

CS was first utilized as a filler for bone defects by Dreesmann in 1892 and, in the first scientific studies undertaken in the 1950s, Peltier demonstrated that CS can be an effective resorbable material for filling bone defects and retaining bone grafts. Peltier noted that CS resorbs rapidly, causes no inflammation, evokes minimal foreign body response, results in normal regeneration of bone, substantial resorption of the CS material, and causes no measurable rise in serum calcium levels. Composites of CS and hydroxylapatite have been shown to induce bone growth (osteoconductivity).

Other related prior art, known to the within inventors, is reflected in U.S. Pat. No. 4,381,947 to Pellico (1983) entitled Settable Alginate Compositions which include Calcium Sulfate; U.S. Pat. No. 5,147,403 (1992) to Gitelis, entitled Prosthesis Implantation Method, which teaches the use of a suspension of CS hemihydrate on a receiving surface of a host bone such that the seating of an orthopedic prosthesis thereon will result in an enhancement of fibroblast growth factor (FGF) at the implant interface.

Later patents which reflect the utility of CS and compounds thereof for use as both a delivery and bone ingrowth medium include U.S. Pat. Nos. 5,366,507 (1994) and 5,569, 308 (1996), both to Sottosanti, and both entitled Method for Use in Bone Regeneration; and U.S. Pat. No. 5,807,567 (1998) to Randolph, et al, entitled CS Controlled Release Matrix for use in Delivery of Antibiotics. U.S. Pat. No. 4,619655 (1986) to Hanker, et al teaches the use of CS as a resorbable scaffold with bone implants. U.S. Pat. No. 5,521, 265 (1993) to Liu teaches surgical cements which include calcium compounds.

It has therefore been known that CS hemihydrate possesses excellent bio-compatibility combined with rapid dissolution which allows use as a carrier for delivery of soluble agents. See Rosenblum, et al, *Material Research Symposium Proceedings, Materials Research Society,* Volume 252 (1992), and Ricci, et al, *Trans Society of Materials* 15:49 (1992); As such, it is known that permanent and resorbable coatings of CS hemihydrate will stimulate in vitro bone ingrowth in an implantable chamber. See also Ricci, et al, Permanent and Resorbable Coatings for Bone Ingrowth into Porous Beaded Surfaces, 23 *Annual Meeting of Society for Biomaterials* (1997). CS therefore has many options for use in bone repair. For example, it may be used alone as a defect filler, as a binder for retention of other materials at a defect site, or as a resorbable barrier to reduce ingrowth from soft tissue near an osseotomy site. Further, the ability of CS to be easily absorbed makes it a suitable delivery vehicle for such materials as growth factors, osteogenic factors and antibiotics. It is currently in use to stimulate bone regeneration, in sinus lift procedures, in oral surgery applications such as filling of cysts or defects left by the removal of impacted wisdom teeth, in endodontic procedures, and in treating periodontal defects. Notwithstanding the above, practicable CS based systems are lacking in many other surgical applications. As such, a number of issues and factors have impeded the development of CS based systems in bone implant and repair procedures. One such problem has been the ingrowth of unwanted tissue into an implant or graft site from adjacent soft tissue to the implant site. This problem has given rise to the concept of a "barrier layer" to protect the graft material or implant from soft tissue disruption. The present invention thereby has, as one objective, the provision of improved barrier methods associated with the use CS systems used in bone tissue regeneration.

A further problem associated with the prior art has been that of synchronizing the rate of in situ bio-resorption of the CS compound/system with the healing process of the adjacent osseous tissue. As above noted, a persistent problem has been that a given CS system will bio-resorb or dissolve too rapidly within the bone thereby outpacing the formation of new bone in human tissue. When this occurs, the effective period of the CS system is significantly diminished. More particularly, when CS is used as a cement to fill a bone void, fracture, or other defect, this material dissolves at a rapid rate, i.e., approximately one millimeter per week from the outside of the defect towards the center thereof. Research of the inventors has shown that this material causes precipitation of calcium phosphate (CP) deposits as it is resorbed by the bone. These precipitates, it has been shown, stimulate and direct the formation of new bone. It is however important for purposes of optimal result that CS, CP, or any other bone repair material stay at the surgical site for a considerable period in order to inhibit soft tissue filling of the defect and to induce proper bone repair. As such, the principal concern and difficulty expressed by practitioners (such as orthopedic and maxiofacial surgeons) using such materials is that they bio-resorb or dissolve too rapidly within the bone and, thereby, outpace the formation of new bone in human patients.

The invention therefore relates to preferable CS combinations or matrices for use with an implant for the repair, augmentation, and other treatment of bone. Such combinations, as set forth below, possesses significant advantages over CS cements and pellets which are currently in clinical use. More particularly, current CS materials are resorbed by human bone within two to seven weeks, depending upon the CS form and the particular surgical site, however, cannot be retained at the site for longer periods. As noted, such material is resorbed faster than it can be replaced by new bone thereby reducing its value to both patient and practitioner. The invention, as such, embodies a CS system particularly formulated and physically configured to be bio-resorbed at controlled rates, thereby substantially matching its rate of resorption to that of the rate of bone repair at specific surgical sites in various applications.

SUMMARY OF THE INVENTION

The instant invention relates to a surgical implant system comprising an implant body and an osseo-stimulative surface applied to or used with said implant body, said surface including a calcium sulfate (CS) compound which is a member selected from the group consisting of CS dihydrate, CS hemihydrate, anhydrous CS and mixtures thereof. The performance and rate of resorption of said osseostimulative surface may be improved or modified through the use of a stabilizing component, a viscosity modifier, a pH modifier, or a cell growth inductive microgeometry. The system is also definable in terms of an in situ system of bone augmentation in which a bio-resorbable CS matrix from a kit is disposed about the surgical implant positioned within an osseotomy site.

The invention, in kit form, will typically include a standalone quantity of a CS compound for use with the surgical implant at the osseotomy site.

Therefore, in view of the above, it is a primary object of the invention to provide an improved article and system for the implantation of prostheses, such as dental implants, and for in situ bone repair.

It is another object to provide an improved means of enhancing osseointegration between a surgical implant or graft and adjacent osseous tissue.

It is a yet further object of the invention to provide a system of the above type which includes an improved barrier layer for the protection of the implant or graft site from disruption by ingrowth of soft tissue, which barrier may resorb after the osseous healing process has been completed.

The above and yet other objects and advantages will become apparent from the hereinafter set forth Brief Description of the Drawings, Detailed Description of the Invention and Claims appended herewith.

BRIEF DESCRIPTION OF THE DRAWINGS

FIG. 1 shows the use of a barrier layer to retard ingrowth between osseous and soft tissue.

FIG. 2 is a cross-sectional breakaway schematic view showing the use of a surgical implant which has been furnished with an osseo-stimulative surface at a pre-operative site.

FIG. 3 is a radial cross-sectional view taken along Line 3—3 of FIG. 2.

DETAILED DESCRIPTION OF THE INVENTION

Figure 1:
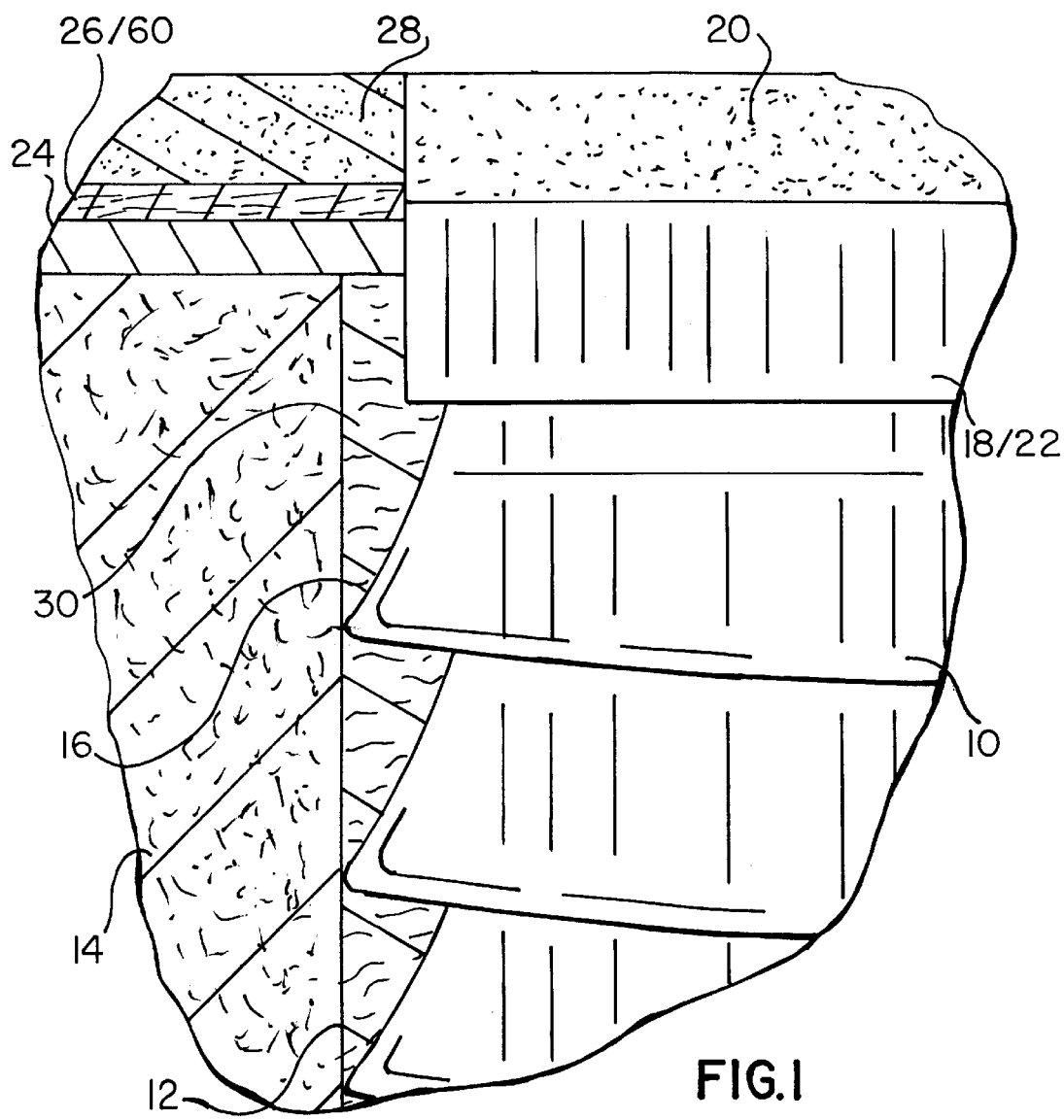
FIG. 1 is a cross-sectional schematic view of a surgical implant furnished, at an operative site, with an osseostiumlative surface to establish bio-integration with surrounding bone tissue. In addition.

The instant invention advances the development of CS related technology in its use of particular combinations of CS, CS compounds and resorbable polymers for use as resorbable implant coatings or cement having characteristics which may be substantially matched to a particular surgical environment within which the implant is to be used. In addition, shortcomings in the utility of prior art forms of CS are addressed through the addition of stabilizers, viscosity modifiers, pH modifiers, and optimizing of the range of the molarity of CS combinations and mixtures so used.

CS naturally occurs in the earth as the mineral gypsum, that is, CS dehydrate. While gypsum and its products differ in purity and form, its major feature is that its water of hydration can be expelled with controlled heating to form CS hemihydrate, this in accordance with the following formula:

$CaSO_4 2H_2O \Longrightarrow CaSO_4 \tfrac{1}{2}H_2O + 1\tfrac{1}{2}H_2O$ (hemidydrate).

The anhydrous form thereof can be produced by heating to higher temperatures in accordance with the following formula:

$CaSO_4 \tfrac{1}{2}H_2O \Longrightarrow CaSO_4 + 1\tfrac{1}{2}H_2O$ (anhydrite)

The addition of water to this material causes setting and a return to the original CS dehydrate.

CS hemihydrate occurs naturally in two forms, designated as the alpha and beta forms of the material. The most common form is the beta form which is used in most commercial grade materials. It employs large amounts of water (approximately 0.6 grams per gram of hemihydrate) in setting and sets to form a less dense material than the alpha form which is used as a dental material also known as a dental stone. The alpha form material uses less water (approximately 0.3 grams per gram of hemihydrate) and sets to form an extremely dense dihydrate. In water, the alpha material is less soluble than the beta form.

There are at least three species of CS which can be used in the present invention. These are CS dihydrate, CS hemihydrate and anhydrous CS. Of these, the most preferred species is calcium sulfate hemidydrate. Among such CS, CS hemihydrate has a solubility which is much higher than that of CS dihydrate. When mixed with water, it will dissolve and recrystallize to form gypsum cement which is mainly CS dihydrate. Because of its relatively high solubility, gypsum cement resorbs quickly. In addition, gypsum cement does not by itself form sufficiently cohesive or adhesive pastes.

Optionally, the CS may further be selected from CS-containing ceramics. Such ceramics should permit the desired interaction between the preferred CS specie and an accelerator/stabilizer component during paste hardening. In fact, any CS containing components which permit this desired interaction is acceptable for use in the present invention. Among the useful CS containing ceramics are CS calcium alkali (such as sodium, potassium and the like), phosphate mixed ceramics and the like, and mixtures thereof.

A number of biocompatible salts have been shown to greatly accelerate setting, that is, decrease the setting time of CS cements when used in relatively low concentration. For example, setting times can be reduced to ten minutes or less, depending upon concentration, using the salts of sodium and potassium. The cations thereof have been found to be most responsible for such acceleration of setting. Conversely, retardation of setting has been observed where organic agents are present such as glycogen, maltose, glycols, hyaluronic acid, collagens, gelatin, succinic acid, and other proteins.

Although the denser alpha and beta forms of CS hemihydrate are preferred, it has been found that any CS having a solubility in pure water at 25 degrees C. in a range of about 0.5 to about $20 \times 10^{-2}$ M can be used for the present purposes.

The within inventors have observed that as CS and its hydrates dissolve in vivo, they elevate the local calcium ion concentration and its surrounding tissue. Calcium ions thus formed react with body fluid to cause local precipitation of calcium phosphate ("CP") bone mineral. Through this mechanism, CP produces new soft granulation tissue that forms about CS as it dissolves and recedes, this as is more fully set forth below. Since CP is stable in an in vivo environment, such CP deposits provide a matrix for the formation and ingrowth of new bone tissue. Thus, such a CP matrix can promote the growth of bone tissue within a defect or, it has been found, stimulate osseointegration between a surgical implant and bone at an osseotomy site. It has however been found that the more soluble CS will dissolve thus driving an in vivo solution to equilibrium in the direction of precipitation of the much less soluble CP, within a matrix or at a surgical site provided for CP deposition. Further, it has been determined that this precipitation process is not always consistent due inter alia to unevenness in the development of granulation tissue about the surgical site.

In response to the above, the inventors have discovered new techniques that employ CS to stimulate bone ingrowth through a bone attachment mechanism similar to the characteristics of hydroxyapatite and bioglasses. These techniques have equal applicability to both orthopedic and dental implants and, as well, may be used in combination with implants that include microgeometric surfaces as are disclosed in our co-pending application Ser. No. 09/500,038 applicable portions of which are incorporated herein by reference.

Particle Size

The CS used in the present invention can be in the form of particles, such as in the granule form or the powder form. Particle sizes preferably are within the range of about 3 microns to about 200 microns or about 400 microns. For the granule form, particle size is more preferably between about 40 mesh to about 80 mesh. Since the cement formation is believed to involve the dissolution of CS and the recrystalization of a less soluble salt, the setting time is a function of the dissolution rate of CS. This, in turn, depends on the type and particle size of the CS-containing component used. Other factors affecting the setting rate are in the amount of water used and the type of the accelerator/stabilizer component used.

A precursor mixture of the present invention preferably may contain about 100 weight parts to about 500 weight parts of CS species per 100 weight parts of an optional accelerator/stabilizer component.

Accelerator/stabilizer Component

An optional accelerator/stabilizer component contemplated by the instant invention is a fluoride component that is preferably selected from at least one of alkali metal fluorides and alkaline earth fluorides. More preferably, the accelerator/stabilizer component is $CaF_2$, KF, NaF, $MgF_2$, or mixtures thereof, or any of the foregoing in combination with NaCl and $K_2SO_4$. Of these, $CaF_2$ is most preferred. Fluoride compounds with elements naturally occurring in bone tissue may also be used. The accelerator/stabilizer components may be in the form of fine powder or granules, having a particle size ranging from a few microns to 20 mesh.

Viscosity Modifiers and Lubricants

Optionally, the CS of the present invention may further include biocompatible fluid lubricants and/or viscosity modifiers. Exemplary lubricant components include glycerol, glycogen, maltose, and the like. Organic polymer based materials, such as polyethylene glycol and hyaluronic acid as well as nonfibrillar collagen, preferably succinylated collagen, may also act as a lubricant. Such lubricants act to modify the viscosity of the compositions, where grouting of the CS is contemplated.

pH Modifiers

Optionally, the surface pH of the setting CS may be decreased by using hydrogen citrate salts or citric acid with alkaline reagents instead of using pure citric acid as the setting reagent. Among the suitable hydrogen citrate salts are sodium dihydrogen citrate, disodium hydrogen citrate, ammonium dihydrogen citrate, diammonium hydrogen citrate, potassium dihydrogen citrate and dipotassium hydrogen citrate. Alternatively, the pH may also be raised by using citric acid with potassium citrate, ammonium citrate, sodium phosphate, disodium hydrogen phosphate, potassium phosphate, and dipotassium hydrogen phosphate. While the pH of concentrated pure citric acid is normally at 2, the pH modified setting reagent should provide an initial solution pH which is much higher than the pure citric acid, reaching a pH of 3 to 5. Therefore, after setting, the surface pH of the setting cement will initially be near 5 and quickly reach 7 or higher upon hardening.

Fillers

Optionally, the CS of the present invention can incorporate biocompatible fillers. Such fillers can be bioresorbable or non-resorbable. The fillers included are preferably substantially inert with respect to the interaction between the preferred CS specie and an accelerator/stabilizer component during hardening. Such fillers include, for example, magnesium oxide, calcium carbonate, alphatricalcium phosphate, beta-tricalcium phosphate, hydroxyapatite, calcium phosphate apatite, bioglass and other calcium phosphate-containing ceramics, tetra calcium phosphate, tricalcium phosphate, calcium phosphate apatite, dicalcium phosphate, magnesium hydroxide and magnesium oxide, and mixtures thereof. The weight ratio of the fillers to the preferred CS species can be up to about 4 to 1. These fillers can be in the form of particles, such as either granules or powder, which preferably have particle sizes in the range of about 3 microns to about 200 microns or about 400 microns.

Preparation of Composition

In the present invention, any two of all the CS, accelerator/stabilizer and optional components can be pre-mixed. To form cement, the premixed CS, e.g., powder is added to the desired amount of water, for example, in the form of a saline solution, to form a paste. This paste becomes viscous and adhesive or cohesive. After a certain time, the paste sets and hardens. Alternatively, the accelerator/stabilizer components are mixed with water first. The CS and other components are then mixed with this aqueous mixture to form a paste. In such case, if the accelerator/stabilizer component is able to dissolve completely in water, a setting solution can be prepared by dissolving the accelerator/stabilizer component first. The pre-mixed CS and other components are then pasted with the setting solution.

In general, the setting time of the present cements can be easily controlled, for example, so that the paste hardens or sets in about 20 minutes or less after the paste, for example, the viscous and cohesive paste, is formed. Beside controllable setting times, the present cements have near neutral or slightly alkaline (pH) surface characteristics. In addition, the composition of the invention can be changed over a relatively wide range so as to provide the flexibility and advantage of controlling the resorption rate.

The techniques of the present invention can be used in orthopedic, maxiofacial and cranial facial surgical applications and in dental applications. These include: 1) a hard tissue replacement material such as bone graft, bone defect filler or bone replacement; 2) ridge augmentation; 3) bone fracture fixation; 4) gluing cement for dentistry and orthopedic surgery; 5) root cement; 6) jaw repair; and 7) bone wax substitute.

Setting Rate

In general, the setting rate depends on the type, crystal morphology and particle size of the calcium-containing component used as a preferred CS specie. In addition, the amount of water, the type and concentration of the accelerator/stabilizer component, and the type and concentration of the strength enhancing component, if any, can also show significant effects on the setting rate. The present surgical cements compositions have workable (reasonable) and controllable setting times, are biocompatible, are easily manipulated, may be formed in situ or in premolded shapes, and have a wide variety of applications.

The strength as well as the setting time of the present CS are directly dependent on the nature of particle size of the optional particular components, the type and amount of the optional setting reagent, and the solid powder to liquid ratio. In general, with other factors constant, the strength increases as the particle size of the particulate components decreases. The setting time increases as the cementing powder to setting regent weight ratio decreases.

The invention may be prepared as a kit, comprising a selected powder and setting reagent which when admixed with aqueous solution will form a paste. The paste will harden in a short time and will reach a pH near 7 or higher. This paste may then be applied to an implant as set forth below.

All valid portions of all U.S. patents or applications cited herein are incorporated herein for the express purpose of enabling one of ordinary skill in the art to practice the instant invention.

With reference to FIG. 1 there is shown, in cross-sectional schematic view, a surgical implant 10 which has been furnished at an operative site 12 for the purpose of establishing bio-integration with surrounding bone tissue 14. An implant of the type of implant 10 includes buttress threads 16 (or other threading) and an integral collar 18 which may consist of an upper part 20 and a lower part 22 thereof. Located above bone tissue 14 is a cortical bone layer 24, an optional bio-resorbable barrier layer 26 (described below) and a gum or soft tissue layer 28.

As may be further noted, an osseo-stimulative surface 30 is applied about implant 10 inclusive of lower part 18 of collar 22 thereof, such surface inclusive of a calcium sulfate ("CS") compound which, as above described, is a member selected from the group consisting of CS dihydrate, CS hemihydrate, anhydrous CS and mixtures thereof. It is to be understood that osseo-stimulative surfaces 30 may be applied to implant 10 before insertion into the osseotomy site or may be applied to the site 12, prior to insertion of the implant. Further, as above noted, the characteristics of the CS compound or matrix may be varied in accordance with a number of parameters, namely, stability, viscosity, pH, and molarity. Further, any of the surfaces of implant 10 inclusive of parts 20 and 22 of the collar 18 may be provided with cell growth stimulative microgeometry in accordance with our co-pending application Ser. No. 09/500,038. The preferred molarity of the CS matrix falls in a range of 0.5 to $20 \times 10^{-2}$ M, and may be furnished in a number of physical forms inclusive of a layer which is physically adhered to the implant 10, a powder, granules, paste, gel, grout, cement, gauze and combinations thereof. However, where an implant exhibits an entirely smooth external geometry, as is the case with an implant 50 (see FIG. 2), an Osseo-stimulative surface 52 is more suitable when physically adhered to the implant at a pre-operative site. It is, however, to be appreciated that a paste, gel or cement form of CS may be applied to an osseotomy site in combination with use of implant 50 and its osseo-stimulative surface 52. It is therefore to be appreciated that, in most clinical applications, combinations of different forms of materials of the CS family will be employed.

Figure 4:
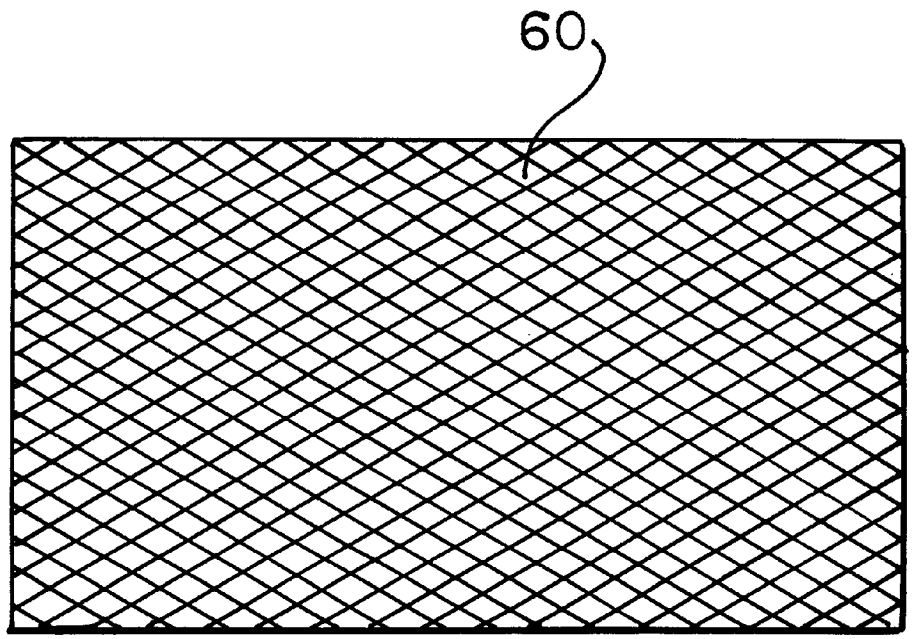
FIG. 4 is a schematic view of a bio-gauze further to the present invention.

An example of a bio-gauze 60 is shown in FIG. 4. Therein it is anticipated that a significant application of such bio-gauze will be as said barrier layer 26 as illustrated in FIG. 1, the function of which is to retard ingrowth of soft tissue 28 into bone 14 and 24 during the period of healing at the bone-implant interface. This barrier layer will, if bio-resorbable, be resorbed by surrounding tissue, however, at a lower rate of resorption than that of osseo-stimulative surface 30 and 52 above-described. If the barrier layer is not resorbable, it would be removed after the healing process of the implant within the osseotomy site has sufficiently progressed.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

We claim:

1. A kit of dental implant materials for bone augmentation and bone defect reparation comprising: (a) an implant body;

and (b) an osseo-stimulative surface, applied to said implant body, said surface including a calcium sulfate ("CS") compound which is a member selected from the group consisting of CS dihydrate, CS hemihydrate, anhydrous CS and mixtures thereof; and (c) a standalone quantity CS compound for in situ application to said implant body, in which said CS compound is a member selected from the group consisting of CS dihydrate, CS hemihydrate, anhydrous CS and mixtures thereof;

wherein said surface comprises a matrix including particles of a resorbable agent for aiding in situ bioresorption of said CS compound at a rate matching with the healing process of the adjacent osseous tissue in order to inhibit soft tissue filling of the defect and to induce proper bone repair; said resorbable agent being a member selected from the group consisting of aliphatic polyesters of an alpha-hydroxy acid derivative, a hydrophilic polymer, an amino derived polymer, poly-vinyl alcohols, polylactides, polyglycolides, polydioxanides, poly-episilon-caprolactones, polymeric salicylates and mixtures thereof.

2. The kit as recited in claim 1 in which said surface further comprises a setting agent.

3. The kit as recited in claim 2 in which said setting agent is an alkaline metal salt solution.

4. The Kit as recited in claim 3 in which said setting agent is a potassium salt solution.

5. The kit as recited in claim 2 in which said surface further comprises a viscosity modifier.

6. The kit as recited in claim 5 in which said viscosity modifier is a member selected from the group consisting of glycogen, maltose, polyethylene glycol, hyaluronic acid, nonfibrillar collagen, succinylated collagen, and mixtures thereof.

7. The kit as recited in claim 2 in which said surface further comprises a pH modifier.

8. The kit as recited in claim 1 in which said standalone quantity of CS is a member consisting of a physically adhered layer, a powder, granules, paste, gel, grout, cement, gauze and combinations thereof.

9. The kit as recited in claim 1 in which said standalone quantity of CS is a member consisting of a physically adhered layer, a powder, granules, paste, gel, grout, cement, gauze and combinations thereof.

* * * * *

UNITED STATES PATENT AND TRADEMARK OFFICE
Certificate

Patent No. 6,582,228 B2                                                                       Patented: June 24, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John L. Ricci, Middleton, NJ (US); Harold Alexander, Short Hills, NJ (US); and Bruce Hollander, Boca Raton, FL (US).

Signed and Sealed this Ninth Day of January 2007.

CORRINE M. MCDERMOTT
                                                                                                               *Supervisory Patent Examiner*
                                                                                                                             Art Unit 3738